United States Patent [19]
Pomeranz

[11] Patent Number: 5,558,093
[45] Date of Patent: Sep. 24, 1996

[54] GUIDEWIRE WITH IMAGING CAPABILITY

[75] Inventor: Mark L. Pomeranz, Los Gatos, Calif.

[73] Assignee: Cardiovascular Imaging Systems, Inc., Sunnyvale, Calif.

[21] Appl. No.: 400,418

[22] Filed: Mar. 2, 1995

Related U.S. Application Data

[63] Continuation of Ser. No. 320,105, Oct. 5, 1994, abandoned, which is a continuation-in-part of Ser. No. 113,972, Aug. 30, 1993, abandoned, which is a continuation-in-part of Ser. No. 846,304, Mar. 5, 1992, abandoned, which is a continuation-in-part of Ser. No. 525,948, May 18, 1990, Pat. No. 5,095,911.

[51] Int. Cl.$^6$ ........................................... A61B 8/12
[52] U.S. Cl. .................. 128/660.03; 128/662.06; 128/772
[58] Field of Search .................... 128/660.03, 660.1, 128/662.03, 662.06, 772; 606/159; 604/99–101

[56] References Cited

U.S. PATENT DOCUMENTS

| | | | |
|---|---|---|---|
| 4,794,931 | 1/1989 | Yock | 128/660.03 |
| 4,951,677 | 8/1990 | Crowley et al. | 128/662.06 |
| 5,000,185 | 3/1991 | Yock | 128/662.03 |
| 5,095,911 | 3/1992 | Pomeranz | 128/662.06 |
| 5,117,831 | 6/1992 | Jang et al. | 128/662.06 |

Primary Examiner—Francis Jaworski
Attorney, Agent, or Firm—Townsend and Townsend and Crew LLP

[57] ABSTRACT

A guidewire imaging catheter includes a catheter body, housing secured to the distal end of the catheter body, a drive cable extending through a central lumen of the catheter body, and an imaging system disposed within the housing and coupled to the drive cable. A fixed guidewire is secured to the distal tip of the housing, and the catheter body is highly flexible while retaining sufficient torsional stiffness to allow the entire catheter to be used as a guidewire. Thus, the imaging guidewire can be used to first image a desired region within a patient's vascular system and subsequently as a guidewire to allow placement of a desired interventional catheter.

13 Claims, 2 Drawing Sheets

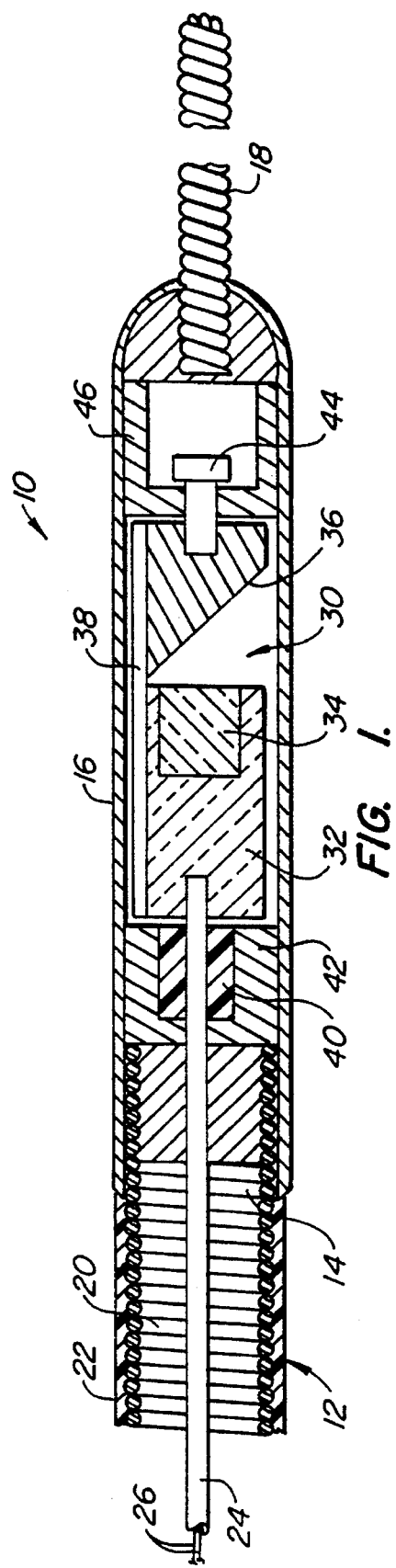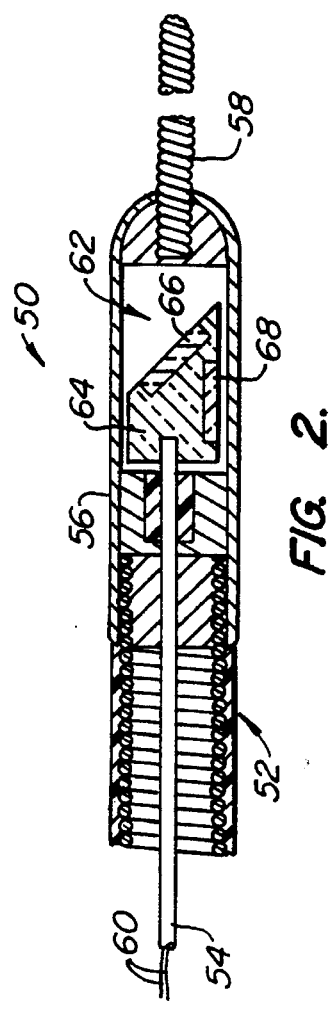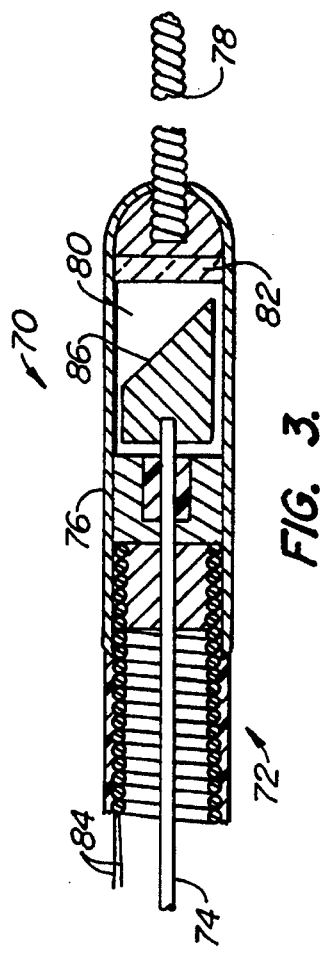

GUIDEWIRE WITH IMAGING CAPABILITY

This is a Continuation of application Ser. No. 08/320,105, filed Oct. 5, 1994, now abandoned which was a CIP of U.S. Ser. No. 08/113,972 (Abandoned), which was a CIP of U.S. Ser. No. 07/846,304; filed Mar. 5, 1992 (Abandoned), which was a CIP of U.S. Ser. No. 07/525,948; filed May 18, 1990 now U.S. Pat. No. 5,095,911.

BACKGROUND OF THE INVENTION

1. Field of the Invention

The present invention relates generally to the construction and use of vascular catheters and, more particularly, to catheters which may be used both as a guidewire for positioning larger catheters and as an ultrasonic imaging catheter.

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed the limbs of the body and coronary blood vessel which feed the heart. When deposits accumulate in localized regions of a blood vessel, blood flow is restricted and the person's health is at serious risk.

Numerous approaches for reducing and removing such vascular deposits have been proposed, including balloon angioplasty, where a balloon-tipped catheter is used to dilatate a region of atheroma; atherectomy, where a blade or other cutting element is used to sever and remove the atheroma; and laser angioplasty, where laser energy is used to ablate at least a portion of the atheroma. In addition to such therapeutic approaches, a variety of techniques for transluminal imaging of atheroma and other diseased regions of a blood vessel has been proposed, including endoscopic imaging techniques and ultrasonic imaging techniques. Common to all such techniques is the use of an intravascular catheter which is positioned at a desired location within the blood vessel to be treated or imaged.

Two alternative approaches may generally be employed to achieve such positioning. In the first approach, the vascular catheter is provided with a "fixed guidewire" secured to its distal end. The fixed guidewire is typically a coiled spring or other elongate resilient member having a preformed, curved tip. The catheter can then be guided through branches within the vascular network by rotating the entire catheter, causing the tip of the guidewire to enter a desired branch as the catheter is moved forward. In the second technique, an entirely separate "movable guidewire" is employed. The movable guidewire is itself a coiled spring or other resilient elongate member and will generally include a curved tip similar to that provided on the fixed guidewires described above. The vascular catheter being positioned includes a guidewire lumen which generally extends down the center of the entire length of the catheter and is sized to receive the movable guidewire. The movable guidewire is first positioned within the vascular system so that its distal end extends beyond the region of interest, and the intravascular catheter is then inserted over the movable guidewire using the guidewire lumen. Such procedures using movable guidewires are commonly referred to as "over-the-wire" insertional techniques.

Recently, ultrasonic imaging catheters have been developed for use in conjunction with various interventional therapies, including angioplasty, atherectomy, laser ablation, and the like. By imaging a diseased region prior to therapy, the treatment can be more precisely directed to both enhance effectiveness and reduce deleterious side effects. Such ultrasonic imaging catheters have generally been introduced prior to therapy, typically using a movable guidewire as just described or a fixed-tip guidewire which is secured to the forward end of the imaging catheter. After imaging has been completed, it has generally been necessary to remove the imaging catheter prior to therapy, although in some cases it has been proposed to provide a particular interventional capability on the imaging catheter itself.

The need to remove the imaging catheter before employing conventional interventional catheters is time consuming and increases the risk that the blood vessel wall will be damaged or that emboli will be accidentally dislodged. Moreover, once removed, the imaging catheter is no longer available for imaging during the therapeutic procedure unless another time-consuming catheter-exchange procedure is employed.

For these reasons, it would be desirable to provide ultrasonic imaging catheters which may also serve as a guidewire for the introduction of larger interventional catheters. Preferably, such imaging guidewire catheters should employ a rotating ultrasonic imaging system where an ultrasonic transducer, a reflective surface, or both, are rotated in order to sweep a continuous ultrasonic signal about the interior of the blood vessel wall.

2. Description of the Background Art

PCT application WO 89/07419 discloses a miniature ultrasonic imaging probe where an ultrasonic transducer is attached to the distal end of a coaxial cable within a holder. The transducer and an acoustic reflector are rigidly maintained within the holder. The ultrasonic transducer cannot be moved within the probe, and it would be necessary to rotate the entire transducer in order to image an annular section of a blood vessel. Such rotation would be deleterious to the blood vessel wall. Probes of the type described in WO 89/07419 are employed inside a protective sheath that remains stationary and covers the entire probe during imaging procedures where the probe is rotated. U.S. Pat. No. 4,794,931, describes an ultrasonic imaging catheter where a rotating transducer, or a rotating mirror in combination with a fixed transducer, is mounted within a housing at the distal end of the catheter. Guidewire catheters are described in various patents, including U.S. Pat. Nos. 4,747,406; 4,724,846; 4,682,607; and 3,416,531. Copending application Ser. No. 07/500,818 filed Mar. 28, 1990 and now U.S. Pat. No. 5,108,411, the disclosure of which is incorporated herein by reference, describes drive cables suitable for use with catheters having rotating distal work elements, where the flexibility of the cable is increased near its distal end.

SUMMARY OF THE INVENTION

A catheter is provided which is capable of both ultrasonic imaging and introducing larger catheters for interventional treatment, such as angioplasty, atherectomy, laser ablation, and the like. The catheter of the present invention comprises a very flexible catheter body having a very small diameter, typically from about 0.3 mm to 1 mm. The bending stiffness constant of the catheter body is very low, typically being in the range from about 1 in-lb-in to 15 in-lb-in, while the torsional stiffness constant is relatively high, typically being in the range from about 0.5 in-lb-in/radian to 7 in-lb-in/radian, so that the distal tip of the catheter can be rotated to facilitate initial positioning within a patient's vascular system. A housing is attached to the distal end of the catheter body, and a drive cable extends through a central lumen in the catheter body from a distal end to a proximal end. To provide high-quality images, a rotating ultrasonic imaging system is disposed within the housing and coupled to the drive. Preferably, the imaging system includes an ultrasonic transducer and a reflective surface which are fixedly interconnected to rotate together as the drive cable is rotated. The reflective surface is disposed to project an ultrasonic signal in a generally transverse direction relative to the housing. In a first alternate embodiment, the ultrasonic transducer is attached directly to the drive cable and disposed to direct the ultrasonic signal in the transverse direction without the need of a reflective surface. In a second alternative embodiment, the transducer is fixedly mounted within the housing, and only a reflective surface is attached to the drive cable. Such a rotating reflective surface can sweep the ultrasonic signal from the transducer in the desired transverse pattern about the blood vessel wall.

In the method of the present invention, the guidewire imaging catheter is first positioned within the patient's vascular system in a manner similar to that employed with conventional guidewires. After initial positioning, the imaging system of the guidewire is used to obtain initial images of the untreated, diseased region within the blood vessel. It is an advantage of the present invention that the image can be obtained without the need to rotate the entire catheter or place the catheter within a protective sheath, as is the case with the catheter described in PCT application WO 89/07419, discussed above. After the first image is obtained, a treatment regimen can be planned and an interventional catheter introduced with the imaging guidewire used as a conventional guidewire. Treatment is performed on the diseased region, again in a conventional manner. During treatment, however, it is possible to periodically produce images of the blood vessel wall to obtain feedback on how the therapy is proceeding. These images can be obtained without the need to remove the interventional catheter, although it will frequently be desirable to move the interventional catheter a short distance away from the region being treated.

BRIEF DESCRIPTION OF THE DRAWINGS

FIG. 1 is a cross-sectional view of the distal end of a preferred guidewire imaging catheter constructed in accordance with the principles of the present invention.

FIG. 2 is a cross-sectional view of the distal end of a first alternate embodiment of a guidewire imaging catheter constructed in accordance with the principles of the present invention.

FIG. 3 is a cross-sectional view of the distal end of a second alternate embodiment of a guidewire imaging catheter constructed in accordance with the principles of the present invention.

DESCRIPTION OF THE SPECIFIC EMBODIMENTS

Figure 4:
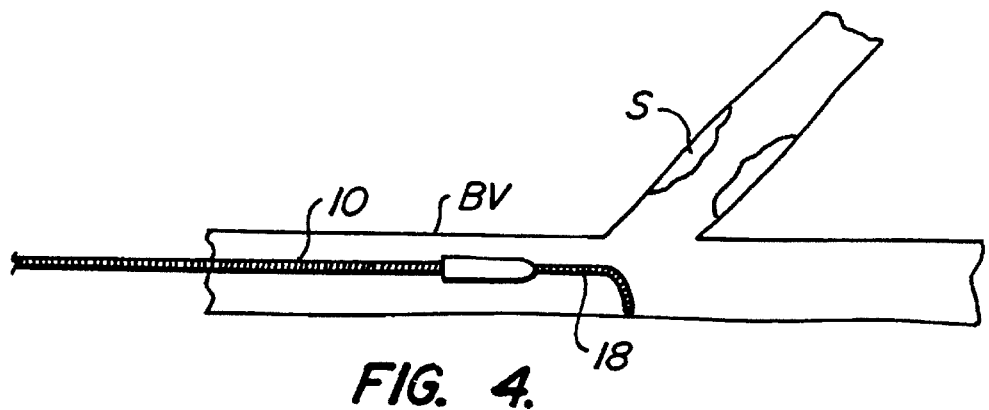
FIGS. 4–7 illustrate the method of the present invention where the guidewire imaging catheter is used to position an angioplasty balloon catheter within a stenosed region in a blood vessel for treatment.
Figure 5:
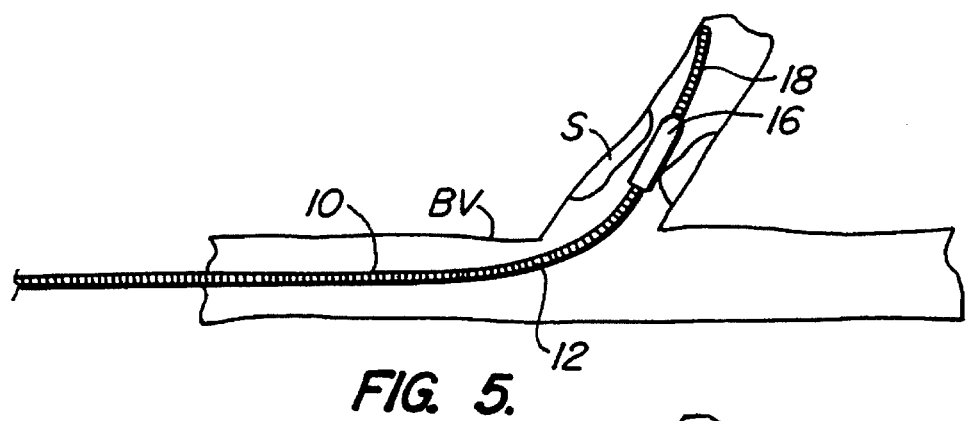

Catheters constructed in accordance with the principles of the present invention will comprise an elongate flexible catheter body having a proximal end, a distal end, and a central lumen extending therebetween. The catheter body comprises a highly flexible structure capable of insertion into and manipulation within a patient's vascular system. The dimensions of the catheter body will depend on use, with the length varying widely, typically being between about 100 cm and 200 cm, usually being between about 125 cm and 175 cm. The catheter body diameter will vary less widely, typically being below about 1 mm in diameter, usually being between about 0.3 mm and 1 mm in diameter, and more usually being between about 0.8 mm and 1 mm in diameter. Such diameters will allow the catheter to be used as a guidewire for most conventional interventional catheters.

As the catheter of the present invention is to be used as a guidewire, it must be very flexible over its length, but also retain sufficient torsional stiffness to allow rotation of the catheter to facilitate positioning and guiding through the vascular system. Typically, the bending stiffness constant of the catheter will be below about 15 in-lb-in, usually being from about 3 in-lb-in to 10 in-lb-in, and preferably being from about 5 in-lb-in to 8 in-lb-in. The torsional stiffness constant will be above about 0.5 in-lb-in/radian, usually being from about 0.5 in-lb-in/radian to 5 in-lb-in/radian, and preferably being from about 1 in-lb-in/radian to 3 in-lb-in/radian. Optionally, the flexibility of the catheter body may vary over its length, with the higher flexibility (lower bending stiffness constant) being present near the distal end of the catheter.

As used herein and in the claims, bending stiffness constant ($K_B$) is defined as $K_B = RFd$, where R=bending radius (in.);

F=deflection force (lb.); and d=length of catheter body section (in.)

The bending stiffness constant may be measured using a conventional 3-point compression tester, such as the Instron Tensile Compression Tester. The catheter body section is placed on a pair of supports spaced apart by a known length (L). A deflection force ($F_d$) is applied to the catheter body section at a location midway between the supports on the resulting deflection measured. The bending radius (R) can then be determined from the measured deflection. Alternatively, the radius can be determined by graphical analysis. In either case, the bending stiffness constant ($K_B$) can then be calculated using the above formula.

As used herein and in the claims, torsional stiffness constant (KT) is defined as:

$K_T = \tau L/\theta$, where $\tau$=applied torque on catheter body section (in-lb)

L=length of catheter body section (in); and $\theta$=angle of wind up over length (radians).

The torsional stiffness constant may be measured by attaching a known length (L) of the catheter body from one section at one end to a goniometer and at the other end to a torque measuring instrument. The goniometer is used to apply a known "wind up" (i.e., number of turns measured in radians) to one end of the catheter body section while the resulting torque is measured at the other end. The torsional stiffness constant ($K_T$) may then be calculated using the above formula.

Such requirements of flexibility and torsional stiffness are best met by coiled constructions, particularly by nested coil constructions having two or more layered coils, which are coated with a polymeric material on the outside, such as teflon, polyurethan, and the like. Conveniently, the catheter body may be formed using conventional techniques of the type which are used for making movable guidewires. Such techniques are well described in the patent and scientific literature. See, for example, U.S. Pat. Nos. 4,747,406; 4,724, 846; 4,682,607; and 3,416,531, the disclosures of which are incorporated herein by reference.

A housing is attached to the distal end of the catheter body. The housing will usually be a continuous shell or sheath which creates an internal volume which is contiguous with the central lumen of the catheter body. Preferably, the shell will be closed but may include openings for specific purposes. The housing both protects and provides mechanical support for the moving components of the ultrasonic imaging system, as described in more detail hereinbelow. Thus, the housing should be formed from an acoustically transparent material to allow for ultrasonic imaging therethrough. The housing will usually be rigid in order to maintain a desired alignment of internal imaging components, but in some cases may possess a small degree of flexibility so long as the operation of the imaging system is not substantially degraded. The housing will usually have a length in the range from about 1 cm to 2 cm, more usually from about 1.4 cm to 1.6 cm, and a diameter in the range from about 0.3 mm to 1 mm, usually from about 0.8 mm to 1 mm.

A drive cable is provided within the central lumen of the catheter body and extends from beyond the proximal end to beyond the distal end thereof. The drive cable must also be axially flexible but torsionally rigid since it must be able to both bend with the catheter body while being able to deliver torque down its entire length to the imaging system, as described in greater detail hereinbelow. The diameter of the drive cable will, however, be substantially less than that of the catheter body, typically being from about 0.25 mm to 0.6 mm, more typically being from about 0.5 mm to 0.6 mm. Methods for forming suitable drive cables are described in U.S. Pat. No. 5,108,411, the disclosure of which is incorporated herein by reference.

An ultrasonic imaging system is disposed within the housing and coupled to the drive cable in order to provide for rotation of at least some of the system components. The basic considerations in constructing an imaging system suitable for use in the catheter of the present invention are described in U.S. Pat. Nos. 4,794,931, and 5,000,185, the disclosures of which are incorporated herein by reference. The constructions described in the U.S. patent and copending patent application may be modified as necessary to adapt the imaging system for use in the much smaller housing of the present invention. The ultrasonic transducer will necessarily be much smaller, typically being shaped cylindrically with a diameter from about 0.3 mm to about 0.9 mm and a length in the range from about 1 mm to 1.6 mm.

Referring now to FIG. 1, a presently preferred embodiment of the guidewire imaging catheter of the present invention will be described. The guidewire imaging catheter 10 includes a catheter body 12 having a distal end 14 and a proximal end (not illustrated). A housing 16 is secured to the distal end 14 of the catheter body 12 and includes a fixed guidewire 18 attached to its distal end. The fixed guidewire 18 will normally include a deviated tip which is useful in guiding the catheter through branches in the vascular system. The construction and use of such deviated-tip fixed guidewires are amply described in the medical and patent literature.

The catheter body 12 includes a flexible wire coil 20 which is coated with a polymeric layer 22 composed of a suitable polymer, such as teflon, polyurethane, and the like.

Other constructions of the catheter body 12 within the parameters described above might also find use. A drive cable 24 extends from the proximal end (not illustrated) of the catheter body 12 to the distal end 14 and into housing 16. The drive cable 24 includes wires 26 which are connected to the ultrasonic imaging system, as described in more detail hereinbelow. The wires 26 serve to interconnect an ultrasonic transducer of the imaging system with the external electronics (not illustrated) needed to both excite the transducer and to interpret ultrasonic energy reflected back from the blood vessel wall.

An ultrasonic imaging system 30 within the housing 16 includes an ultrasonic transducer 32 having a piezo-electric element 34 at its distal end. The transducer 34 and piezoelectric element 34 are aligned to project ultrasonic energy generally in the forward axial direction, where such energy will encounter a reflective surface 36. The reflective surface 36 is inclined at an angle of about 45° relative to the axial direction so that the ultrasonic energy will be reflected radially outward from the housing 16. It will be appreciated that by adjusting the angle of surface 36, the projected energy can be directed forwardly or rearwardly of the true radial direction.

The ultrasonic transducer 32 and reflective surface 36 are rigidly attached to each other by a strut member 38. The proximal or rearward end of the transducer 32 is mounted on the distal end of drive cable 24, and the distal end of drive cable 24 in turn is mounted within a proximal bearing 40 which is secured within a bearing retainer 42 located generally at the distal end of housing 16. Similarly, the distal end of reflective surface 36 is mounted on a locking pin 44 which is received within a distal bearing 46. In this way, the rigid assembly of the transducer 32, reflective surface 36, and strut member 38, can be rotated between the bearing members 40 and 46 by rotation of drive cable 24. This is a preferred manner of construction because of the extended distance between the transducer 34 and the exterior of housing 16, providing for improved near field imaging capability. Additionally, the mechanical joining of the mirror 36 to the transducer 34 improves their mutual alignment and enhances the imaging capability.

Referring now to FIG. 2, an alternate construction of the guidewire imaging catheter of the present invention will be described. The catheter 50 includes a catheter body 52, a drive cable 54, and a housing 56, each of which is generally the same as the corresponding component described with reference to FIG. 1. Catheter 50 further includes a fixed guidewire 58 and a pair of connecting wires 60 which may also be identical to those earlier described. The imaging system 62 employed by the catheter 50, however, differs from that earlier described in that no reflective surface is employed. Instead, a rotating transducer 64 is attached to rotate with drive cable 54 and includes a pair of piezoelectric elements 66 and 68. The first piezo-electric element 66 is oriented at an angle of about 45° relative to the axial direction so that it is able to project and receive ultrasonic energy directed in a forward conical pattern about the housing 56. The second piezo-electric element 68 is oriented to project and receive ultrasonic energy in a generally radial direction relative to the housing 56 so that an annular scan path may be achieved. The use of rotating ultrasonic transducers to provide imaging is described in greater in U.S. Pat. Nos. 4,794,931, and 5,108,411, the disclosures of which have previously been incorporated herein by reference.

Referring now to FIG. 3, a second alternate embodiment of the imaging catheter of the present invention will be described. The catheter 70 includes catheter body 72, a drive cable 74, and a housing 76, each of which may be the same or similar to the corresponding component described in connection with the embodiment of FIG. 1. The housing 76 further includes a fixed guidewire 78 at its distal tip, and the construction of the guidewire may be the same as that previously described. An imaging system 80 within the housing 76 includes a fixed ultrasonic transducer 82 located proximate the distal end of the housing 76 and is oriented to project ultrasonic energy generally in the proximal or rearward axial direction. The transducer 82 is externally connected through a pair of wires 84 which are brought rearward through the catheter body 72. A reflective surface 86 is mounted at the distal end of the drive cable 74 and is inclined so that it is able to reflect the ultrasonic energy in a generally radial direction as the reflective surface is rotated.

Referring now to FIGS. 4–7, the method of the present invention will be described. In particular, a blood vessel BV, having a region of stenosis S is located within a branch thereof, will be imaged using the imaging guidewire 10 described above. Imaging guidewire 10 is introduced to the blood vessel BV by conventional techniques and brought to the region proximate the branch under fluoroscopic control. As the branch is approached (FIG. 4), the catheter 10 may be rotated until the fixed guidewire tip 18 enters the desired branch of the blood vessel having the stenosed region S.

After the guidewire tip 18 enters the branch, the catheter 10 is moved forward so that the housing 16 is able to enter the stenosed region S. The guidewire tip 18 will then extend beyond the stenosed region, while the catheter body 12 extends backward through the main branch of the blood vessel to the point of entry. The imaging system 30 within the housing 16 may then be used to image the stenosed region by sweeping the ultrasonic signal radially about the housing 16, typically at a rate in the range from about 50 rpm to 2000 rpm, preferably from about 600 rpm to 1500 rpm. One or more cross-sectional images of the stenosed region S may then be obtained by the methods described in U.S. Pat. Nos. 4,794,931 and 5,000,185, the disclosures of which have previously been incorporated herein by reference.

Figure 6:
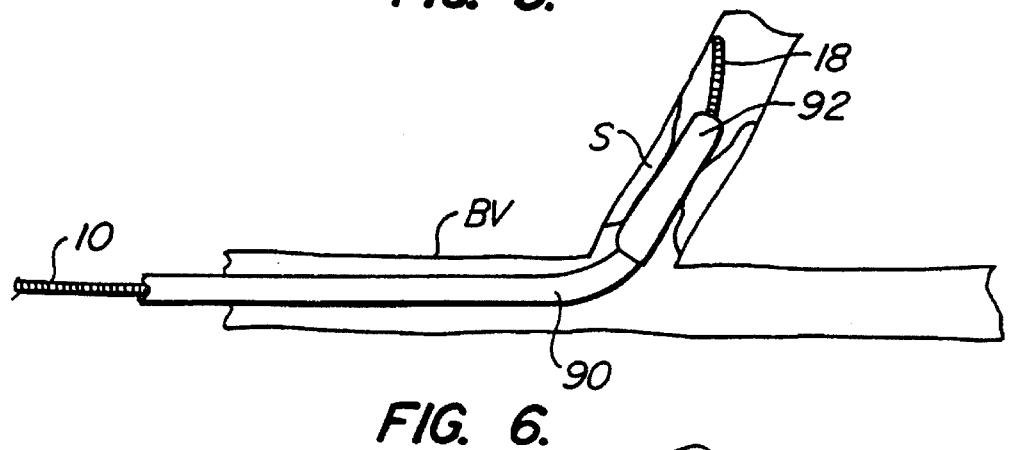
Figure 7:
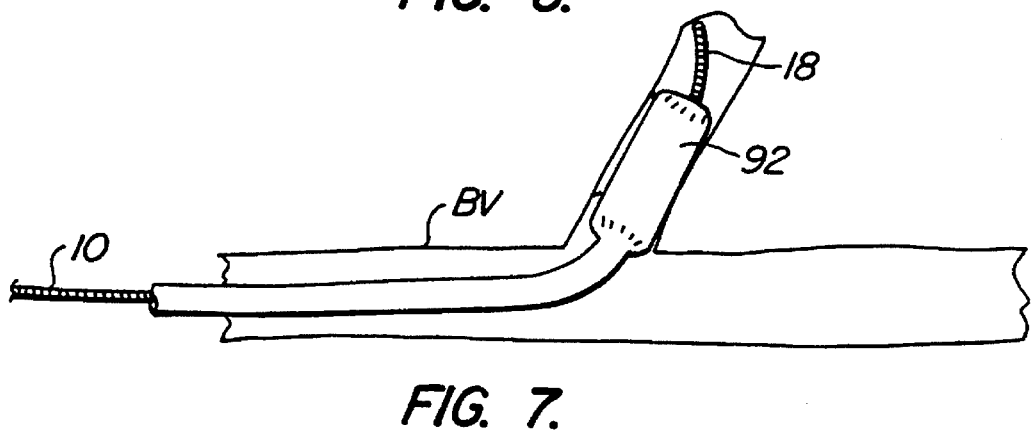

After the nature of the stenosed region S has been determined to the desired extent, a method of therapeutic treatment can be selected. For example, it may be desirable to treat the stenosed region S with a dilatation balloon catheter. In that case, a dilatation balloon catheter 90 having a distal balloon 92 may be introduced over the imaging guidewire 10 in a generally conventional manner. The dilatation balloon catheter 90 will include a central guidewire lumen having dimensions compatible with the imaging guidewire 10 so that the balloon 92 may be brought within the stenosed region S (FIG. 6). By then inflating the dilatation balloon 92, as illustrated in FIG. 7, the stenosed region S may be compressed and blood flow through the blood vessel BV restored. After the balloon 92 is deflated, the catheter 90 may be moved back slightly to again expose the housing 16 so that the region S may again be imaged. Based on such imaging, the need to further treat the blood vessel can be assessed.

Although the foregoing invention has been described in some detail by way of illustration and example for purposes of clarity of understanding, it will be obvious that certain changes and modifications may be practiced within the scope of the appended claims.

What is claimed is:

1. An improved vascular imaging and interventional method wherein a stenosed region in a blood vessel is treated with an interventional catheter, said improvement comprising imaging the stenosed region using an imaging guidewire which is movably disposed within the interventional catheter, wherein the interventional catheter is used for treating the stenosed region.

2. An improved method as in claim 1, comprising extending an imaging system of the imaging guidewire distally beyond the distal end of the interventional catheter in order to image the stenosed region.

3. An improved method as in claim 2, comprising positioning an imaging system of the imaging guidewire within the interventional catheter while the stenosis is being treated.

4. An improved method as in claim 1, comprising generating a generally axial ultrasonic imaging signal and rotating a reflective surface within the imaging guidewire, where the reflective surface is disposed to transversely reflect the generally axial ultrasonic imaging signal.

5. A method as in claim 4, wherein the reflective surface is rotated at a rate in the range from about 50 rpm to 2000 rpm.

6. A method as in claim 1, comprising rotating an ultrasonic transducer within the imaging guidewire catheter, where the transducer is disposed to project an ultrasonic imaging signal transversely relative to the catheter.

7. A method as in claim 1, wherein the interventional catheter is initially introduced over the imaging guidewire.

8. A method for imaging and treating a diseased region within a blood vessel, said method comprising the following steps:

treating the diseased region with an interventional catheter;

moving a drive cable relative to the interventional catheter to position an ultrasonic transducer at the diseased region, wherein the drive cable is unconnected to the interventional catheter; and rotating the drive cable within the interventional catheter to scan the diseased region of the blood vessel with the ultrasonic transducer.

9. A method as in claim 8, wherein the drive cable and ultrasonic transducer are rotated within a guidewire positioned within the interventional catheter.

10. A method as in claim 9, wherein the guidewire remains stationary relative to the blood vessel while the interventional catheter is moved thereover.

11. A method as in claim 9, wherein the interventional catheter remains stationary relative to the blood vessel while the guidewire is moved therein.

12. A method as in claim 8, wherein at least one treating step is performed prior to performing the moving step.

13. A method as in claim 8, wherein the treating step comprises inflating a balloon on the interventional catheter to dilate a stenosed region of the blood vessel.

* * * * *